(12) United States Patent
Eppelheimer et al.

(10) Patent No.: US 9,315,296 B2
(45) Date of Patent: Apr. 19, 2016

(54) PACKAGING FOR BULKY ARTICLES WITH FALSE SIDE GUSSET

(71) Applicant: Kimberly-Clark Worldwide, Inc., Neenah, WI (US)

(72) Inventors: Reed Carlson Eppelheimer, Appleton, WI (US); Stephen Robert Kehn, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 117 days.

(21) Appl. No.: 14/134,865

(22) Filed: Dec. 19, 2013

(65) Prior Publication Data

US 2015/0175312 A1   Jun. 25, 2015

(51) Int. Cl.
*B65D 30/00* (2006.01)
*B65D 33/04* (2006.01)
*B65D 33/14* (2006.01)
*B65D 77/14* (2006.01)
*B65D 30/18* (2006.01)

(52) U.S. Cl.
CPC ............... *B65D 31/00* (2013.01); *B65D 31/08* (2013.01); *B65D 33/04* (2013.01); *B65D 33/14* (2013.01); *B65D 77/14* (2013.01)

(58) Field of Classification Search
CPC ........ B65D 31/10; B65D 31/00; B65D 31/08; B65D 33/2591; B65D 33/2533; B65D 33/04; B65D 33/14; B65D 75/5866; B65D 77/14; Y10S 383/906
USPC .................. 383/120, 906, 907, 37, 2
See application file for complete search history.

(56) References Cited

U.S. PATENT DOCUMENTS

| | | | | |
|---|---|---|---|---|
| 5,104,235 A | * | 4/1992 | Bronstrup | B65D 31/10 383/10 |
| 5,392,589 A | * | 2/1995 | Buchanan | B65B 61/18 229/125.42 |
| 5,547,284 A | * | 8/1996 | Imer | B31B 37/00 383/104 |
| 6,030,123 A | * | 2/2000 | Mitarai | B65D 31/10 24/585.12 |
| 6,164,826 A | * | 12/2000 | Petkovsek | B65D 31/10 383/120 |
| 6,186,663 B1 | * | 2/2001 | Ausnit | B31B 19/90 24/30.5 R |
| 6,398,412 B2 | * | 6/2002 | Wedi | B65D 33/2533 383/120 |

(Continued)

FOREIGN PATENT DOCUMENTS

| | | |
|---|---|---|
| EP | 1 184 294 A2 | 3/2002 |
| JP | 2001-171685 A | 6/2001 |
| JP | 2008-007148 A | 1/2008 |

*Primary Examiner* — J. Gregory Pickett
*Assistant Examiner* — Peter Helvey
(74) *Attorney, Agent, or Firm* — Kimberly-Clark Worldwide, Inc.

(57) ABSTRACT

A new package for storing bulky goods is disclosed. The package is formed from a bag having a width and depth at its base portion and meeting at a top edge, the top edge having no depth. Due to the top edge having no depth, the width of the material on the top portion of the package extends out further than the width of the material on the base portion. To create a package having streamlined aesthetic that looks nice on a shelf, the excess material in the top portion of the bag is folded into the interior of the bag to form a false side gusset. To allow for such folding the bag, in desirable embodiments, side edges of a first and second web forming the bag angle inward at between about 30 degrees and about 60 degrees at a top portion transition point on the bag.

11 Claims, 4 Drawing Sheets

(56) References Cited

U.S. PATENT DOCUMENTS

| | | | | |
|---|---|---|---|---|
| D471,437 S * | 3/2003 | Ichikawa | ................ | D9/709 |
| 6,805,485 B2 * | 10/2004 | Hogan | ................ | B65D 31/10 383/120 |
| 7,036,713 B2 * | 5/2006 | Lee | ................ | B65D 5/74 229/115 |
| 7,204,641 B2 * | 4/2007 | Stolmeier | ................ | B65D 31/10 383/120 |
| 7,976,220 B2 * | 7/2011 | Brauer | ................ | B65D 31/10 383/120 |
| 8,899,836 B2 * | 12/2014 | Wedi | ................ | B65D 31/10 383/120 |
| 2004/0146224 A1 * | 7/2004 | Piotrowski | ................ | B65D 31/10 383/64 |
| 2006/0078233 A1 * | 4/2006 | Winiecki | ................ | B31B 19/86 383/104 |
| 2006/0285781 A1 * | 12/2006 | Zoss | ................ | B65D 75/58 383/120 |
| 2010/0142858 A1 * | 6/2010 | Kruse | ................ | B65D 31/10 383/5 |
| 2012/0269469 A1 | 10/2012 | Long et al. | | |
| 2013/0004627 A1 | 1/2013 | Kerr et al. | | |

* cited by examiner

PACKAGING FOR BULKY ARTICLES WITH FALSE SIDE GUSSET

BACKGROUND

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garments look and feel as much as possible like "regular" underwear to promote an improved sense of normalcy to the wearer who suffers from incontinence or enuresis. Additionally, purchasers and users of such products are frequently embarrassed about their condition and about having to purchase products to deal with their incontinence or enuresis condition.

Currently, the most common method for obtaining incontinence and enuresis underwear is by purchasing relatively large bags in retail stores. Such conventional packages of incontinence and enuresis underwear are opaque or mostly opaque, which some purchasers may perceive as overly "diaper-like" or too strongly connoting the presence of a personal care absorbent product directed to a urinary condition. Such conventional packaging bears little resemblance to the packaging in which durable clothing is sold. There is a need for a package of incontinence or enuresis underwear that better resembles a package of durable underwear so as to improve the feeling of normalcy for the purchaser/user. There is also a need for a package of incontinence or enuresis underwear that allows the potential purchaser to see selected features of the underwear, such as, for example, cloth-like material used to make the underwear, elastic waistbands, and back-label indicators.

Attempts have been made in the art to provided windowed packages to allow consumers to inspect the absorbent garments contained within the sealed packages prior to purchase. However, the prior art does not optimally provide for targeted display and/or obscurement of particular features of pants, particularly with larger underwear such as incontinence and enuresis underwear, some of which frequently require multiple folds in both directions to efficiently configure the underwear for commercial packaging and sale.

Durable clothing and other bulky goods are often sold in a package system that combines a rectangular carton inside a poly bag to allow for displaying targeted displays of features while still maintaining the products in the correct position in the package. Many bags also require a header banner for branding and hanging the package on retail hooks.

When a standard flat bag is placed on a 3-dimensional carton or bulky goods, the result is prominent "dog ears" protruding from the sides of the bag header. This is due to the fact that the flat bag width must be significantly wider than the front face panel of the carton or good, in order to accommodate the depth dimension of the carton. This causes significant difficulties in merchandising the finished packs on shelf, as packs interfere with one another when they are placed side-by-side. The aesthetics are also generally considered to be undesirable.

One way of eliminating the protruding "dog ears" is to utilize a side gusset bag. This method of bag formation tucks excess poly in the top seal, and creates a much narrower top banner, while maintaining the necessary bag circumference to accommodate the carton. This problem with this approach is that side gusset bags are typically used in bulk, loose fill applications such as dog food or lawn fertilizer, and as such the only machines currently available in market to produce this style of bag require extremely heavy and rigid laminate film types. This look and feel is decidedly ill-suited to the merchandising of underwear and absorbent-type products.

A packaging structure is needed that can be produced using soft films which allows a 3-dimensional or bulky contents to fit in a bag for storing bulk goods without undesirable aesthetics.

SUMMARY

To better meet the above-described unmet needs in the art, a new package is disclosed herein. Generally, a new package for storing bulky goods is disclosed. The package is formed from a bag having a width and depth at its base portion and meeting at a top edge, the top edge having no depth. Due to the top edge having no depth, the width of the material on the top portion of the package extends out further than the width of the material on the base portion. To create a package having streamlined aesthetic that looks nice on a shelf, the excess material in the top portion of the bag is folded into the interior of the bag to form a false side gusset. To allow for such folding the bag extends out at a certain angle in the top portion to allow for proper and streamlined folding of the bag.

In one embodiment, a package is constructed from bag sealed together at a pair of side edges. The bag may be formed from a first web and second web sealed together at the pair of side edges. The bag includes a base portion having a depth and a first width at the base portion forming a cavity between the first web and second web. The bottom edges of the bag portion of the bag may be folded together to provide a bottom to the bag. The bag also includes a top portion. The top portion of the bag extends from a top portion transition point adjacent the base portion of the bag to a top edge. The bag has no depth at a top edge of the bag and a second width at the top portion transition point, wherein the second width is greater than the first width. The excess material formed in the top portion of the bag is folded and tucked into the interior of the bag to provide a bag having a clean appearance on shelf. Typically, to provide a clean package on the shelf, the side edges of the first web and second web angle inward at between about 30 degrees and about 60 degrees at a top portion transition point on the bag. In a desirable embodiment, the side edges of the first web and second web angle inward at between about 40 degrees and about 50 degrees at a top portion transition point on the bag. In another desirable embodiment, the side edges of the first web and second web angle inward at about 45 degree angle provides for a desirable fold appearance.

In another embodiment, a package is constructed from a bag and a housing portion to store articles. The housing portion includes a housing depth, housing width, and housing height, the housing portion having an opening at its top. The bag formed from a first web and a second web sealed together at a pair of side edges. The bag includes a base portion having a depth and a first width at the base portion forming a cavity between the first web and second web. The bottom edges of the bag portion of the bag may be folded together to provide a bottom to the bag. The bag also includes a top portion. The top portion of the bag extends from a top portion transition point adjacent the base portion of the bag to a top edge. The bag has no depth at a top edge of the bag and a second width at the top portion transition point, wherein the second width is greater than the first width. The excess material in the top portion of the bag is folded and tucked into the interior of the bag to provide a bag having a clean appearance on shelf. Typically, to provide a clean package on the shelf, the side edges of the first web and second web angle inward at between about 30 degrees and about 60 degrees at a top portion transition point on the bag. In a desirable embodiment, the side edges of the first web and second web angle inward at between about 40 degrees and about 50 degrees at a top portion transition point on the bag. In another desirable embodiment, the side edges of the first web and second web angle inward at about 45 degree angle provides for a desirable fold appearance.

In desirable embodiments, the housing portion has an opening at a top of the housing portion for displaying and removing articles. A feature of the articles stored within the housing extends through the opening of the housing portion and is visible to a consumer.

In other desirable embodiment, the bag includes a header strip. In some embodiments, a hole in the header strip enabling the package to be hung on a pin or rod on a display rack in a first shelf configuration. The header strip has a header strip width that may desirably be substantially similar in width to the first width of the base portion of the package. In other embodiments, a header strip width that may be greater or smaller in width than the first width of the base portion of the package.

Use of a housing portion within the bag allows for two types of storage configurations of the packaging. A hole in the header strip enables the package to be hung on a pin or rod on a display rack in a first shelf configuration. In this embodiment, the housing portion would have a flat bottom enabling the package to be placed on a shelf in a second shelf configuration. Having a package with two types of shelf configuration provides more flexible position on the store shelf.

DETAILED DESCRIPTION

Reference to the Figures shall be made in describing various aspects and embodiments of the invention. It should be noted that the embodiments depicted in the Figures and described herein are merely representative examples of the pants and package of the invention. The various aspects and embodiments of the present invention are suitable for use with any goods. In some embodiments, adult incontinence pants, prefastened disposable diapers, disposable swim pants, disposable training pants, disposable enuresis garments, and the like may be used with the package.

Generally, a new package for storing bulky goods is disclosed. The package is formed from a bag having a width and depth at its base portion and meeting at a top edge, the top edge having no depth. Due to the top edge having no depth, the width of the material on the top portion of the package extends out further than the width of the material on the base portion. To create a package having streamlined aesthetic that looks nice on a shelf, the excess material in the top portion of the bag is folded into the interior of the bag to form a false side gusset. To allow for such folding the bag extends out at a certain angle in the top portion to allow for proper and streamlined folding of the bag.

Figure 1:
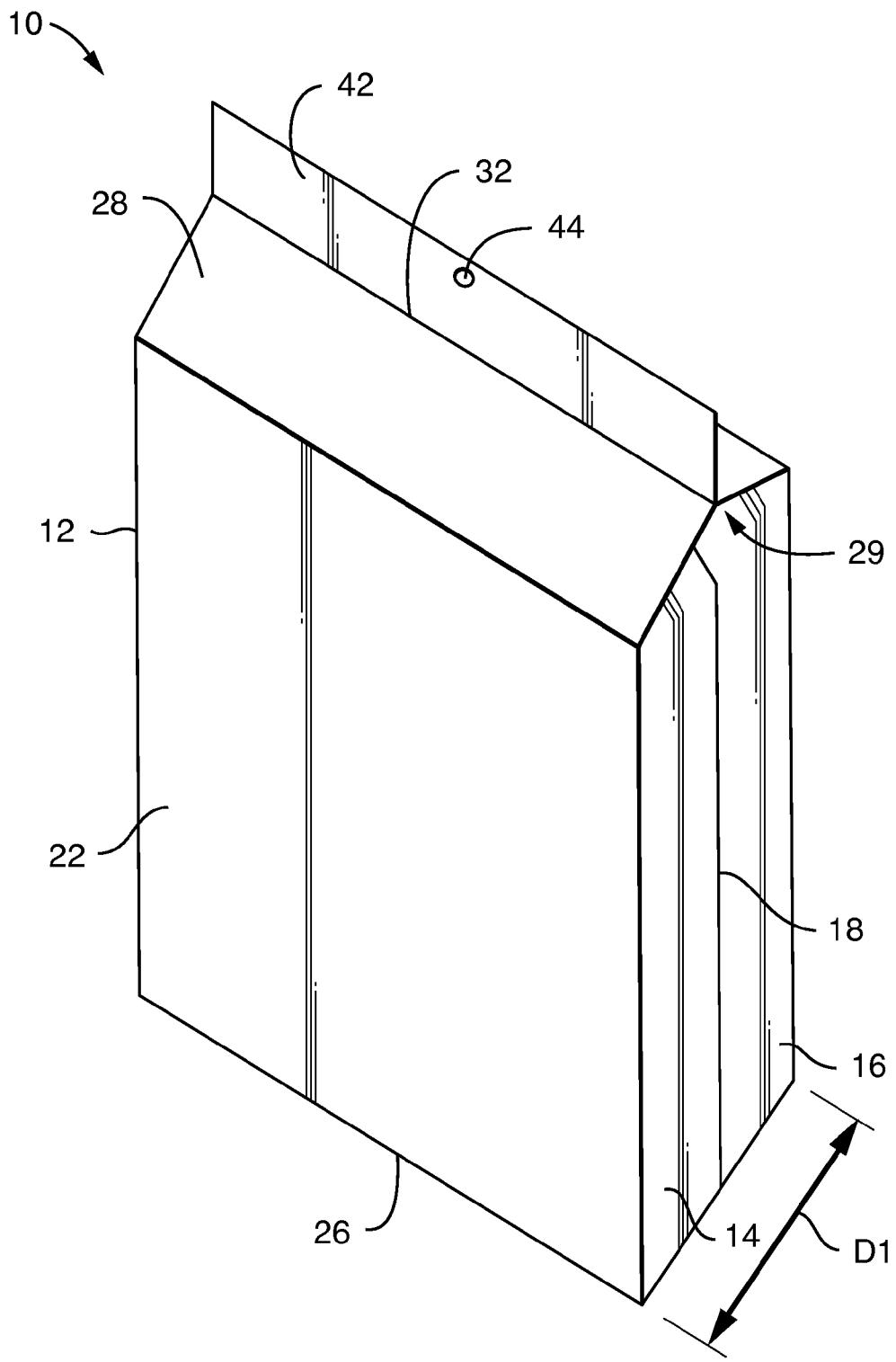
FIG. 1 representatively illustrates perspective view of one exemplary embodiment of the package of the present invention.
Figure 2:
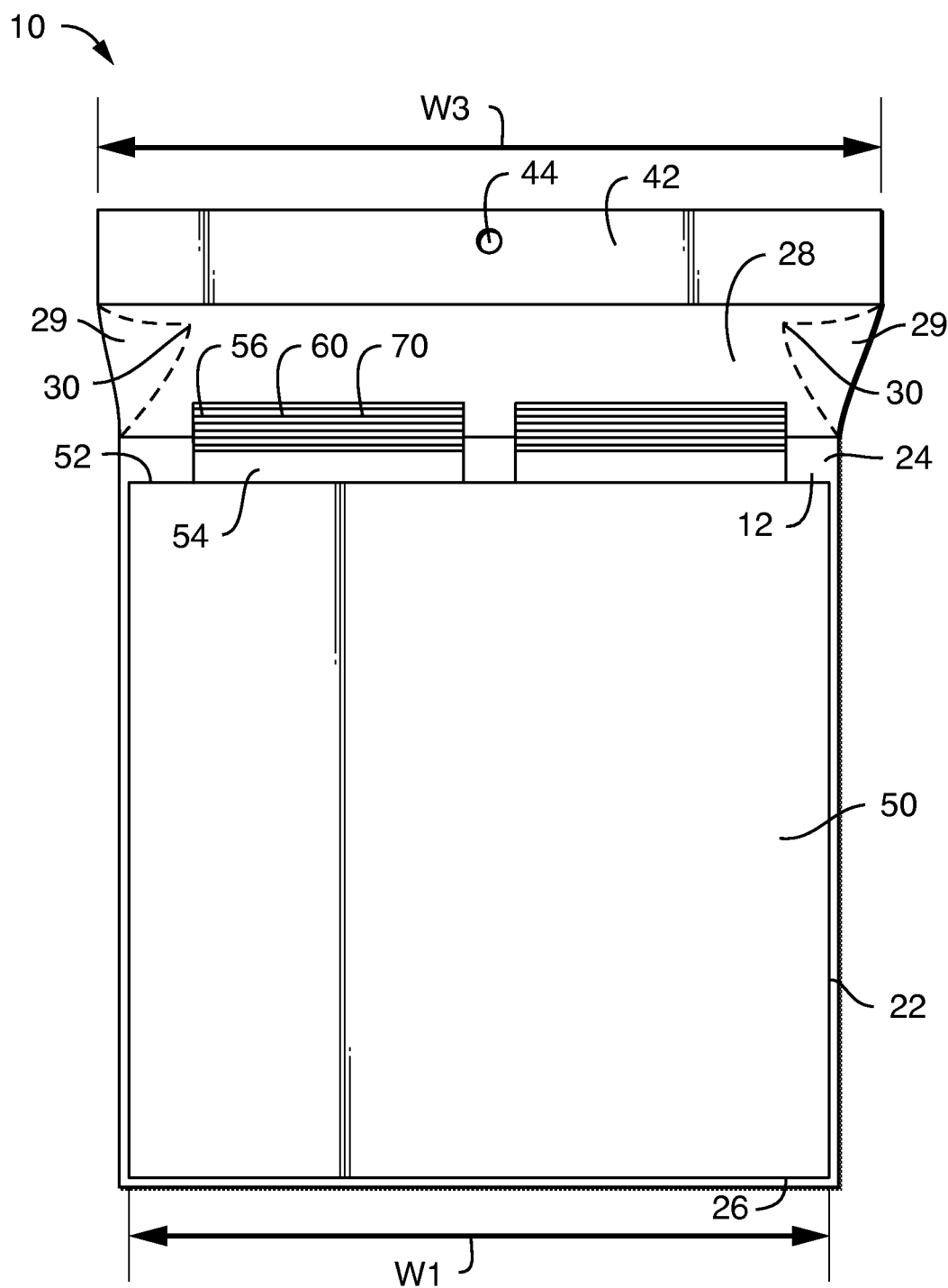
FIG. 2 representatively illustrates a front plan view of the package shown in the embodiment of FIG. 1 including a housing portion and articles disposed therein.
Figure 3:
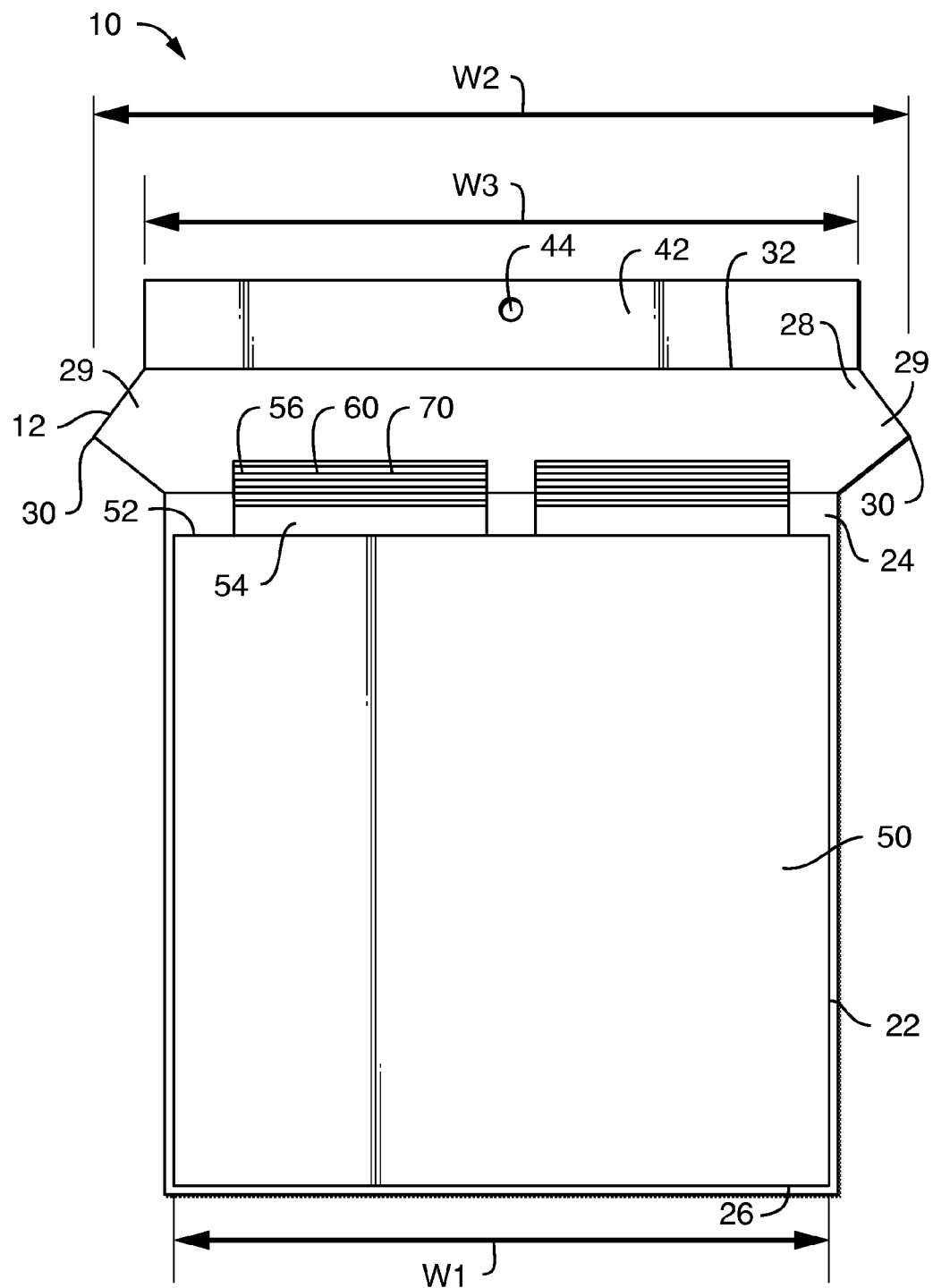
FIG. 3 representatively illustrates a front plan view of the package shown in the embodiment of FIG. 1 including a housing portion and articles disposed therein prior to tucking in the excess material formed in the top portion of the bag into the exterior of the bag.

Turning to FIGS. 1-3, a package 10 is constructed from bag 12. The bag may be formed a tube from at least one material web and sealing tube at a pair of side edges. As illustrated, the bag is formed from a first web 14 and a second web 16 sealed together at a pair of side edges 18, 20. The first and second web 14, 16 may be sealed at the side edges 18, 20 by any means known to those skilled in the packaging art. For example, in one embodiment, the first and second web 14, 16 will be sealed with pinch seal, or an adhesive seal. When sealing with an adhesive, a hot melt adhesive is preferably used for sealing the side edges of the web. Ultrasonic or heat sealing may also be used to seal the side edges 18, 20 of the first and second web 14, 16 with or without a pinch seal and with or without adhesive. In addition, any combination of sealing techniques may also be used to seal the side edges 18, 20 of the first and second web 14, 16 together.

In exemplary embodiment, each of the first and second web 14, 16 may be formed from a durable, flexible material suitable for such containment and storage of materials. Examples of suitable materials for the first web and second web include, but are not limited to paper, aluminum foil, metalized films, coated films, printed films, co-extruded films, polyester films, polyolefin based films, white polyolefin based films, polyamide based films, copolymer films, multi-layer polymer films and films containing various polymer blends. Preferably, the first web and second web is polyolefin based, such as a monoweb polymer. One desirable embodiment would be polypropylene. Other examples include polyethylene and blends of polypropylene and polyethylene and separate layers of polymers, and other intermediate extrusion layers can be utilized with the separate woven polypropylene layer and the propylene outer layer. These polymers can be blended in combination or used in separate, distinct sheets.

In some embodiments, the first web 14 and second web 16 are formed from the same materials. In other embodiments, the first web 14 and second web 16 are formed from different materials.

The constructed bag 12 includes a base portion 22 having a depth D1 and a first width W1 at the base portion 22 forming a cavity 24 between the first web 14 and second web 16. Once filled with the contents of the package 10, the bottom edges of the first and second web 14, 16 of the bag 12 may be folded together to provide a bottom 26 to the bag 12.

The bag 12 also includes a top portion 28. The top portion 28 of the bag 12 extends from a top portion transition point 30 adjacent the base portion 22 of the bag 12 to a top edge 32. The bag 12 is sealed at the top edge 32. The first and second webs 16, 18 may be sealed at the top edge 32 by any means known to those skilled in the packaging art. For example, in one embodiment, the web will be sealed with pinch seal, or an adhesive seal. When sealing with an adhesive, a hot melt adhesive is preferably used for sealing the side edges of the web. Ultrasonic or heat sealing may also be used to seal the side edges of the bag with or without a pinch seal and with or without adhesive. In addition, any combination of sealing techniques may also be used to seal the top edge 32 of the first and second web 14, 16 together.

As illustrated in FIG. 3, the bag 12 has no depth at a top edge of the bag and a second width W2 at the top portion transition point 30, wherein the second width W2 is greater than the first width W1. As discussed above, due to the top edge 32 having no depth, the excess material 29 from the top portion 28 of the bag 12 extends out further than the width of the material on the base portion 22 of the bag 12. To create a package 10 having streamlined aesthetic that looks nice on a shelf, that excess material 29 of the top 28 portion of the bag 12 is folded into the interior or cavity 24 of the bag 12 as illustrated in FIGS. 1 and 2.

Figure 4:
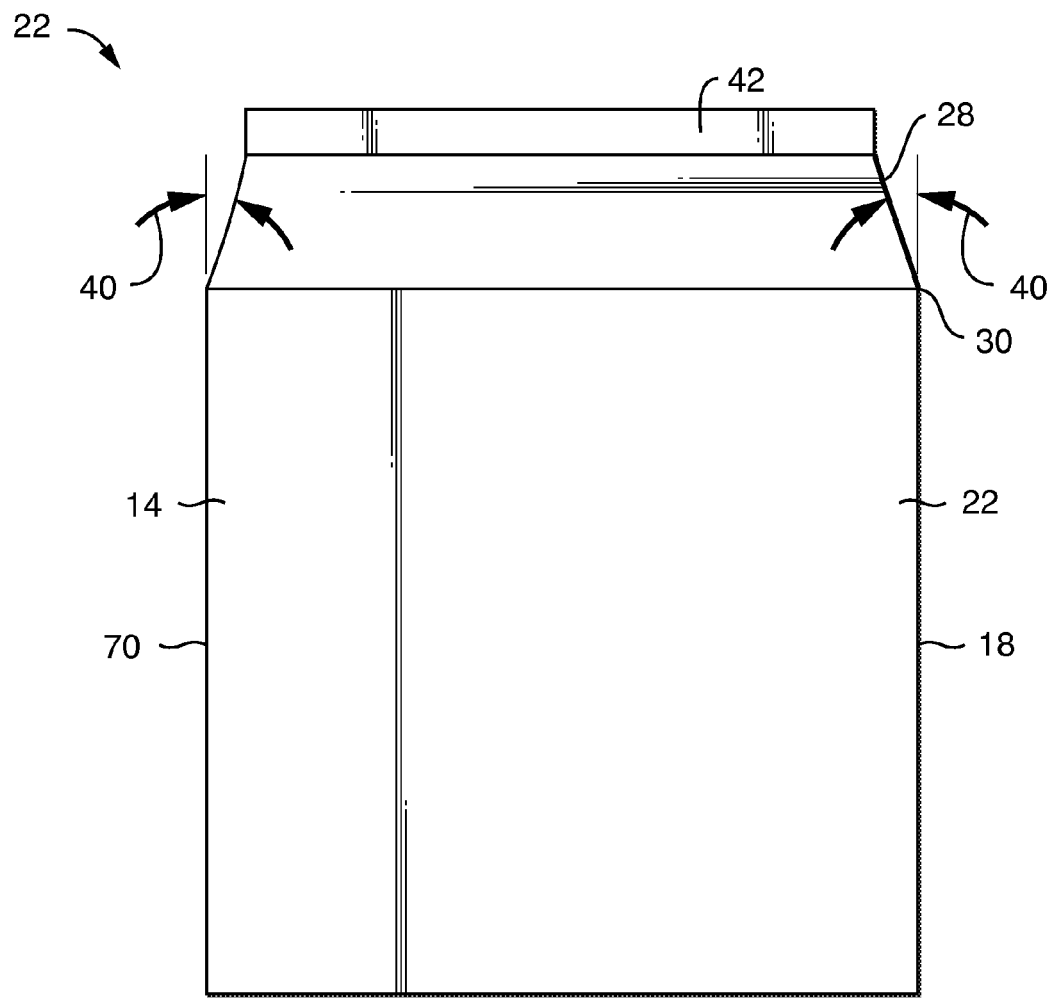
FIG. 4 representatively illustrates a view of the bag utilized in the package, the bag laid out longitudinally in a laid-flat condition, prior to the folding the bottom edges into to provide the depth to the package shown in the embodiment of FIG. 1.

To allow for the material of the top portion 28 of the bag 12 to fold properly into the interior or cavity 24 of the bag 12, the first and second webs 14, 16 have a specifically designed structure. As illustrated in FIG. 4, the formation of the side edges 18, 20 of both the first and second web 14, 16 is the key to getting the polymer film to fold into an inverted corner and lay flat is the angle at which the side of the bag 12 is cut. Typically, to provide a clean package 10 on the shelf, the side edges 18, 20 of the first web and second web 14, 16 angle inward at a transition angle 40 between about 30 degrees and about 60 degrees at a top portion transition point 30 on the bag 12 to the top edge 32 of the bag 12. In another embodiment, the side edges 18, 20 of the first web and second web 14, 16 angle inward at a transition angle 40 between about 40 degrees and about 50 degrees at a top portion transition point 30 on the bag 12 to the top edge 32 of the bag 12. In one desirable embodiment, the side edges 18, 20 of the first web 16 and second web 18 angle inward at a transition angle 40 of about a 45 degree angle providing for a desirable fold appearance.

While the soft film is somewhat forgiving in the range of about 15 degrees, any angle beyond that range will start to show undesirable puckering at angles of less than 40 degrees, and incomplete tucking at angles greater than 50 degrees. Incomplete tucking or undesirable puckering of the package results in a package that is less appealing to a consumer on shelf. Therefore, having a correct transition angle 40 in formation of the first and second webs 14, 16 allowing for folding of the bag 12 is critical to providing a package 10 capable of storing bulky goods and having a header strip for proper shelf aesthetics.

In desirable embodiments, the first and second webs 14, 16 forming the bag 12 are transparent materials, allowing a consumer to see the contents of the package 10 for inspection. In other embodiments, the first and second webs 14, 16 are opaque.

Adjacent the top edge 32 of the bag 12 is an integral header strip 42. In some embodiments, a hole 44 in the header strip 42 enabling the package 10 to be hung on a pin or rod on a display rack in a first shelf configuration. The header strip has a header strip width W3 that may desirably be substantially similar in width to the first width W1 of the base portion 22 of the package 10. In other embodiments, a header strip width W3 that may be greater or smaller in width than the first width W1 of the base portion 22 of the package 10.

In some embodiments, the package 10 includes a housing portion 50 to store the articles. The housing portion 50 includes a housing depth, housing width, and housing height, the housing portion having an opening 52 at its top. The housing portion 50 of the package 10 may be formed of any suitable packaging material known to those skilled in the art, such as, for example, paper, plastic film, paperboard, corrugated board, flexible polymeric material, semi-rigid plastic, or combinations thereof. In one embodiment, the housing portion 50 at least in part comprises a carton, such as a paperboard carton. The housing portion 50 may optionally include one or more inserts disposed within the housing portion 50, such as a paperboard insert.

In a desirable embodiment, the housing portion 50 has an opening 52 at the top of the housing portion 50 for displaying an article or good. The articles or goods 54 are positioned within the housing portion 50 such the at least one article 54 extends above the height of the housing portion 50, and such that at least a feature 56 of the article 54 is visible through the transparent bag 12. For example, a feature 56 of the articles 54 extends through the opening 52 of the housing portion 50 and is visible to a consumer.

As illustrated in the figures, the package 10 may further include a plurality of articles disposed within the housing portion 50. In particular embodiments, the articles may include disposable absorbent pants or durable absorbent pants for use with disposable absorbent pads. Examples of these types of articles suitable for incorporation into particular embodiment of the present invention include those disclosed in U.S. application Ser. No. 13/547,974 filed by Evenson et al. on Jul. 12, 2012, U.S. application Ser. No. 13/933,235 filed by Vignali et al. on Jul. 2, 2013, and U.S. application Ser. No. 13/933,260 filed by Evenson et al. on Jul. 2, 2013, the contents of each of which is hereby incorporated by reference to the extent consistent herewith. Examples of disposable absorbent pants having certain aspects suitable for incorporation into particular embodiments of the present invention include those disclosed in U.S. Pat. No. 5,745,922 issued May 5, 1998 to Rajala et al., U.S. Pat. No. 6,240,569 issued Jun. 5, 2001 to Van Gompel et al., U.S. Pat. No. 6,702,798 issued Mar. 9, 2004 to Christoffel et al., and U.S. Pat. No. 7,604,624 issued Oct. 20, 2009 to Veith et al., the contents of each of which is hereby incorporated by reference to the extent consistent herewith. Note that the disposable absorbent pants could be provide in a permanently "closed" (i.e., pull-on style) configuration, a releasably and refastenably "closed" configuration, or an "open" (i.e., non-prefastened) configuration—any of which could be used in conjunction with the various embodiments of the present invention. While illustrated as a garment, any object or article requiring the package to have bulk may be stored within the package described herein.

Referring to FIGS. 2-3, in particular embodiments at least one garment 60, such as at least two pants, of the plurality of articles is positioned within the housing portion 50 such the at least one garment 60 extends above the height of the housing portion 50, and such that at least a portion of the a feature 56 of the garment 60 is visible through the transparent bag. In this way, it can in certain embodiments be possible to highlight for a consumer the waistband region 70 of the garment or article. The feature 56 of the garments 60 that is illustrated through the package is selected from cloth-like material used to make the underwear, elastic waistbands, and back-label indicators. Without intending to be limiting, the present inventors have discovered that these particular dimensional relationships can in particular embodiments optimize the balance between displaying desired features 56 of the product through the package bag 12.

The housing portion 50 may also be used to store components of the goods that are undesirable for the consumer to see or require more discretion. For example, in the type of product with having both a durable absorbent pants for use with disposable absorbent pads, the absorbent pads may be stored within the housing and not visible to a consumer. If stored within the housing portion 50, the absorbent pads cannot be seen and provide more discretion to a consumer who purchases them at the store normalizing the purchase and providing a better consumer experience.

In addition, use of a housing portion 50 within the bag 12 allows for two types of storage configurations of the packaging. A hole in the header strip enables the package to be hung on a pin or rod on a display rack in a first shelf configuration.

In this embodiment, the housing portion 50 would have a flat bottom enabling the package 10 to be placed on a shelf in a second shelf configuration. Having a package 10 with two types of shelf configurations provides more flexible positioning on the store shelf.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A package for storing goods, the package comprising:
   a housing portion having a housing depth, housing width, and housing height, the housing portion having an opening at its top;
   a bag formed from a first web and a second web sealed together at a pair of side edges, the bag having a base portion and a top portion, wherein the side edges of the first web and second web angle inward between about 40 and about 50 degrees at a top portion transition point on the bag, the bag having a bag depth and a first bag width at the base portion forming a cavity between the first web and second web for storing the housing portion, the bag having no depth at a top edge of the bag and a second bag width at the top portion transition point, wherein the second bag width is greater than the first bag width, wherein excess material in the top portion of the bag is folded and tucked into the interior of the bag;
   a header strip formed across the top edge of the bag having a header strip width; and
   wherein a good stored within the housing extends through the opening of the housing portion and is visible to a consumer.

2. The package of claim 1 wherein the sides edges angle inward at between about 40 degrees and about 50 degrees at a top portion transition point on the bag.

3. The package of claim 1 wherein the sides edges angle inward at about 45 degrees at the top portion transition point.

4. The package of claim 1 wherein the first bag width is substantially similar to the header strip width.

5. The package of claim 1 wherein the header strip width is greater or smaller than the first bag width.

6. The package of claim 1 wherein the housing portion is selected from paper, plastic film, paperboard, corrugated board, flexible polymeric material, semi-rigid plastic, or combinations thereof.

7. The package of claim 1 wherein the housing portion has an opening at the top of the housing portion for displaying articles, wherein a feature of the articles extends through the opening of the housing portion and is visible to a consumer.

8. The package of claim 7 wherein the article comprises at least a first pant of positioned within the housing portion such that the first pant extends through the opening, and such that at least a portion of a waistband region of the first pant is visible through the bag.

9. The package of claim 7 wherein the feature of the articles is selected from cloth-like material used to make the underwear, elastic waistbands, and back-label indicators.

10. The package of claim 1 further comprising a hole in the header strip enabling the package to be hung on a pin or rod on a display rack in a first shelf configuration.

11. The package of claim 1 wherein the first and second web comprises transparent materials.

\* \* \* \* \*